(12) United States Patent
Tegels

(10) Patent No.: US 9,149,264 B2
(45) Date of Patent: Oct. 6, 2015

(54) CAM DRIVEN COMPACTION TUBE FOR VASCULAR CLOSURE DEVICE

(75) Inventor: Zachary J. Tegels, Otsego, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 1087 days.

(21) Appl. No.: 12/901,285

(22) Filed: Oct. 8, 2010

(65) Prior Publication Data

US 2012/0089177 A1 Apr. 12, 2012

(51) Int. Cl.
| | | |
|---|---|---|
| *A61B 17/08* | (2006.01) | |
| *A61B 17/00* | (2006.01) | |
| *A61B 17/04* | (2006.01) | |
| *A61B 17/06* | (2006.01) | |
| *A61B 17/29* | (2006.01) | |

(52) U.S. Cl.
   CPC ......... *A61B 17/0057* (2013.01); *A61B 17/0482* (2013.01); *A61B 17/06123* (2013.01); *A61B 2017/00637* (2013.01); *A61B 2017/00654* (2013.01); *A61B 2017/00659* (2013.01); *A61B 2017/0414* (2013.01); *A61B 2017/0417* (2013.01); *A61B 2017/0496* (2013.01); *A61B 2017/2915* (2013.01)

(58) Field of Classification Search
   CPC ........... A61B 17/0057; A61B 17/0401; A61B 17/0482; A61B 2017/00637; A61B 17/06123; A61B 2017/2915; A61B 2017/00654; A61B 2017/0417; A61B 2017/0496; A61B 2017/0414; A61B 2017/00659
   USPC .......................................... 606/213, 232, 103
   See application file for complete search history.

(56) References Cited

U.S. PATENT DOCUMENTS

| | | | |
|---|---|---|---|
| 5,021,059 A * | 6/1991 | Kensey et al. | 606/213 |
| 5,662,681 A * | 9/1997 | Nash et al. | 606/213 |
| 6,045,569 A | 4/2000 | Kensey et al. | |
| 6,090,130 A | 7/2000 | Nash et al. | |
| 7,618,436 B2 | 11/2009 | Forsberg | |
| 7,618,438 B2 | 11/2009 | White et al. | |
| 7,749,247 B2 | 7/2010 | Tegg | |
| 8,298,259 B2 * | 10/2012 | Terwey | 606/213 |
| 8,465,519 B2 * | 6/2013 | Terwey | 606/213 |

(Continued)

FOREIGN PATENT DOCUMENTS

WO   2006124238 A2   11/2006

OTHER PUBLICATIONS

International Preliminary Report on Patentability for International Application No. PCT/US2011/001660, mailed Apr. 9, 2013 (8 pp.).

*Primary Examiner* — Corrine M McDermott
*Assistant Examiner* — Jing Ou
(74) *Attorney, Agent, or Firm* — Holland & Hart

(57) ABSTRACT

A method and apparatus for sealing a puncture or incision formed percutaneously in a tissue. The apparatus including an anchor, a sealing plug, a filament connected between the sealing plug and the anchor, a compaction member assembly, a spool and a driving plate. The compaction member assembly being disposed adjacent the sealing plug and structured and arranged to apply an axially directed compressive force to automatically compact the sealing plug toward the anchor. The spool has a portion of the filament wound thereon. The driving plate being connected to the spool and having a cam surface portion. The cam surface portion is arranged to contact a proximal end of the compaction member assembly upon rotation of the spool to advance a distal end of the compaction member assembly.

14 Claims, 11 Drawing Sheets

(56) References Cited

U.S. PATENT DOCUMENTS

| | | |
|---|---|---|
| 2005/0085851 A1 | 4/2005 | Fiehler et al. |
| 2006/0229673 A1 | 10/2006 | Forsberg |
| 2006/0229674 A1 | 10/2006 | Forsberg |
| 2006/0265006 A1* | 11/2006 | White et al. .................. 606/232 |
| 2006/0265007 A1* | 11/2006 | White et al. .................. 606/232 |
| 2007/0032823 A1 | 2/2007 | Tegg |
| 2007/0255314 A1* | 11/2007 | Forsberg ...................... 606/213 |
| 2008/0071311 A1* | 3/2008 | White et al. .................. 606/232 |

\* cited by examiner

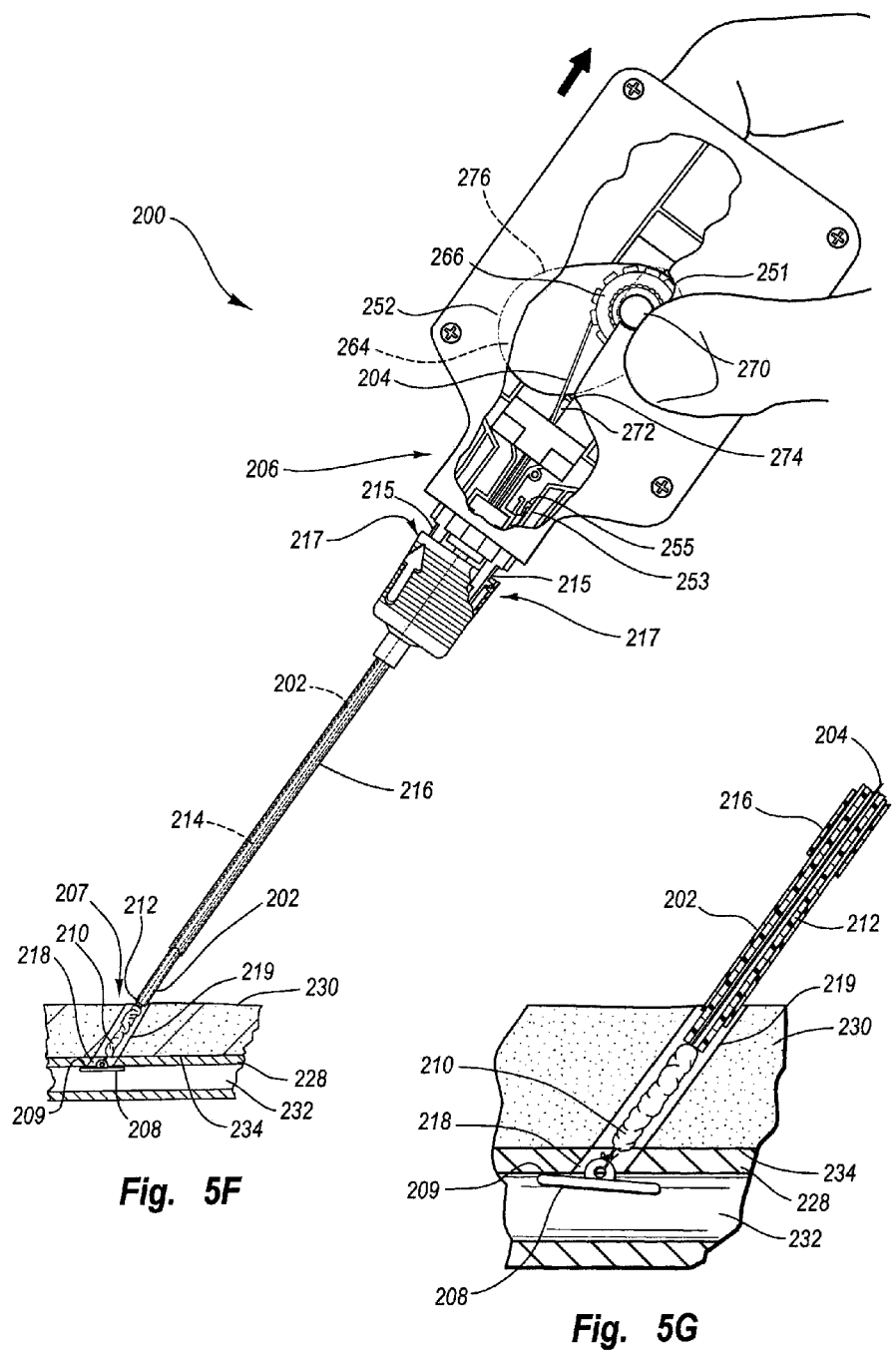

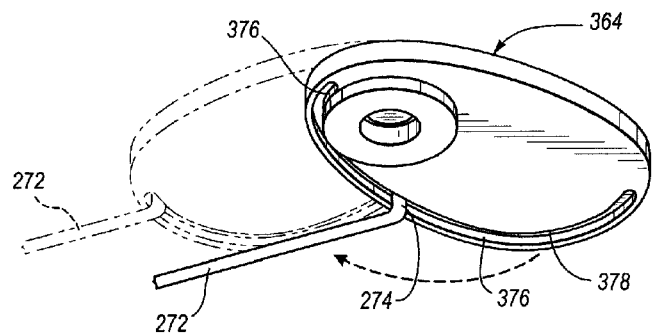
Fig. 7
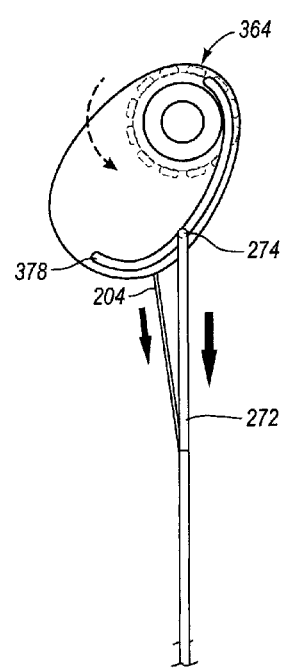
Fig. 8A
Fig. 8B
Fig. 8C

CAM DRIVEN COMPACTION TUBE FOR VASCULAR CLOSURE DEVICE

TECHNICAL FIELD

The present disclosure relates generally to medical devices and more particularly to devices for sealing punctures or incisions in a tissue wall.

BACKGROUND

Various surgical procedures are routinely carried out intravascularly or intraluminally. For example, in the treatment of vascular disease, such as arteriosclerosis, it is a common practice to invade the vessel and insert an instrument (e.g., a balloon or other type of catheter) to carry out a procedure within the vessel. Such procedures usually involve the percutaneous puncture of the vessel so that an insertion sheath may be placed in the vessel and thereafter instruments (e.g., catheters) may pass through the sheath to an operative position within the vessel. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices, such as those described in U.S. Pat. Nos. 6,090,130 and 6,045,569, which are hereby incorporated in their entireties herein by this reference.

Typical closure devices such as the ones described in the above-mentioned patents place a sealing plug at the tissue puncture site. Successful deployment of the sealing plug, however, requires that it be manually ejected from within a device sheath and compacted down to an outer surface of the tissue puncture using a compaction tube. The compaction procedure cannot commence until the device sheath (within which the compaction tube is located) has been removed so as to expose the compaction tube for manual grasping. Under certain conditions, removal of the sheath prior to compacting the sealing plug may cause the sealing plug itself to be displaced proximally from the tissue puncture, hindering subsequent placement of the sealing plug, and resulting in only a partial seal and associated late bleeding from the tissue puncture. Accordingly, there is a need for improving the mechanism for deployment of the sealing plug at the site of a tissue puncture.

SUMMARY

The present disclosure meets the above-described needs and others. Specifically, the present disclosure provides methods and systems for closing internal tissue punctures. However, unlike prior systems, the present disclosure provides automatic compaction to a sealing plug as the closure device is retracted. In addition, the present disclosure allows the automatic compaction system to disengage, facilitating full retraction of the closure device and easy separation of the sealing plug from the remainder of the closure device.

In one of many possible embodiments, the present disclosure provides a tissue puncture closure device that includes an anchor, a sealing plug, a filament, a compaction member assembly, a spool, and a driving plate. The filament is positioned between the sealing plug and the anchor. The compaction member assembly is structured and arranged to apply an axially directed compressive force to automatically compact the sealing plug toward the anchor, and has a distal end and a proximal end. The spool has a portion of the filament wound thereon. The driving plate is connected to the spool and has a cam surface portion that is arranged to contact the compaction member assembly upon rotation of the spool to advance the distal end of the compaction member assembly.

The cam surface portion may be defined around a periphery of the driving plate. The cam surface portion may be defined within a slot feature of the driving plate. The compaction member assembly may further include a drive follower positioned at the proximal end of the compaction member assembly and exposed for contact by the cam surface portion. The compaction member assembly may include a compaction tube and a compaction tube driver arranged end-to-end, wherein the compaction tube defines the distal end of the compaction member assembly. The cam surface portion may include a constant radius portion and a variable radius portion.

Another aspect of the present disclosure relates to a tissue puncture closure device for partial insertion into and sealing of a tissue puncture in an internal tissue wall accessible through a percutaneous incision. The tissue puncture closure device includes an anchor, a sealing plug, a filament, a compaction assembly, a storage spool, and a driving plate. The anchor is disposed on a distal side of the internal tissue wall. The sealing plug is disposed on a proximal side of the internal tissue wall. The filament is connected to and anchored at a distal end to the anchor and sealing plug, wherein the sealing plug is slidable and cinchable along the filament toward the anchor to close the tissue puncture. The compaction assembly is disposed on the filament and arranged to drive the sealing plug along the filament distally towards the anchor. The storage spool has a proximal end of the filament wound thereon. The driving plate is connected to the storage spool and has a cam surface arranged to apply a variable driving force to the proximal end of the compaction assembly upon rotation of the storage spool.

The driving plate may be connected to the storage spool by a releasable clutch. The cam surface may include a constant radius portion and a variable radius portion. The storage spool and driving plate may be arranged coaxially. The driving plate may be coupled to the compaction assembly. Withdrawing the tissue puncture closure device from the tissue puncture with the anchor bearing against the internal tissue wall may unwind the filament from the storage spool. The storage spool may rotate the driving plate and the driving plate drives the compaction assembly to directly or indirectly provide a compaction force to the sealing plug. The cam surface may directly contact the compaction assembly.

Another aspect of the present disclosure relates to a method of sealing a tissue puncture in an internal tissue wall of a vessel accessible through a percutaneous incision. The method may include providing a closure device having an anchor, a sealing plug, a filament positioned between the sealing plug and the anchor, a compaction member, a spool having a portion of the filament wound thereon, and a driving plate that is connected to the spool and has a cam surface portion. The method further includes inserting the anchor through the tissue puncture and withdrawing the closure device from the tissue puncture with the anchor positioned within the vessel. Withdrawing the closure device rotates the spool, and rotating the spool rotates the driving plate to advance the compaction member and compact the sealing plug toward the anchor.

Rotating the driving plate may contact the cam surface portion with a proximal end portion of the compaction member to apply a variable force to the compaction member. The closure device may further include a compaction member assembly that includes a compaction tube having a distal end arranged adjacent to the sealing plug, and a compaction tube driver having a distal end abutting a proximal end of the compaction tube. Rotating the driving plate contacts the cam surface portion with a proximal end of the compaction tube driver.

Another aspect of the present disclosure relates to a method of sealing a tissue puncture in an internal tissue wall accessible through a percutaneous incision. The method includes providing a tissue puncture closure device comprising a filament connected at its distal end to an anchor and to a sealing plug located proximal of the anchor for disposition and anchoring about the tissue puncture, a compaction member assembly, and a driving plate having a cam surface portion. The method also includes inserting the tissue puncture closure device into the percutaneous incision, deploying the anchor into the tissue puncture, at least partially withdrawing the tissue puncture closure device from the percutaneous incision, and automatically compacting the sealing plug toward the anchor upon withdrawal of the tissue puncture closure device from the internal tissue wall puncture with the driving plate and compaction member assembly. Automatically compacting includes rotating the driving plate to contact the cam surface portion with the compaction member assembly to advance a distal end of the compaction member assembly. The method further includes cutting the filament to leave the anchor and sealing plug at the tissue puncture.

The compaction member assembly may include a drive follower at a proximal end thereof, and the cam surface portion contacts the drive follower to advance the compaction member assembly. The tissue puncture closure device may also include a spool about which a portion of the filament is wound, wherein the spool is connected to the driving plate. Automatically compacting may include rotating the spool thereby rotating the driving plate.

Additional advantages and novel features will be set forth in the description which follows or can be learned by those skilled in the art through reading these materials or practicing the examples disclosed herein.

BRIEF DESCRIPTION OF THE DRAWINGS

The accompanying drawings illustrate various embodiments of the present disclosure and are a part of the specification. The illustrated embodiments are merely examples and do not limit the scope of the invention.

FIG. 5F is a side view of the tissue puncture closure device of FIG. 5A shown engaged with a vessel in a third position with a carrier tube retracted to expose a sealing plug adjacent to the tissue puncture.

FIG. 5G is a detailed inset of FIG. 5F.

FIG. 7 is a perspective view of another example driving plate in accordance with the present disclosure.

FIGS. 8A-8C illustrate the driving plate of FIG. 7 in three different rotated positions to advance a compaction tube driver of the tissue puncture closure device.

Throughout the drawings, identical reference numbers designate similar, but not necessarily identical, elements.

DETAILED DESCRIPTION

Figure 1:
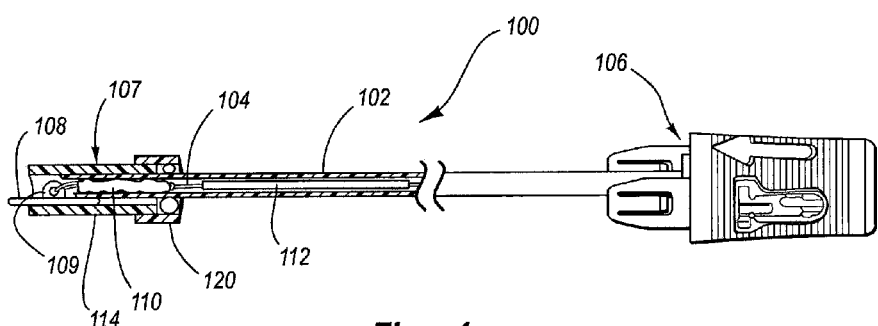
FIG. 1 is a partial cut-away view of a tissue puncture closure device according to the prior art.

As mentioned above, vascular procedures are conducted throughout the world and require access to a vessel through a puncture. Most often, the vessel is a femoral artery. To close the puncture following completion of the procedure, many times a closure device is used to sandwich the puncture between an anchor and a sealing plug. However, sometimes the sealing plug is difficult to eject from the sealing device and may not properly seat against an exterior situs of the arteriotomy. If the plug does not seat properly against the arteriotomy, there is a potential for elongated bleeding.

The present disclosure describes methods and apparatuses that facilitate sealing plug ejection and proper placement of the sealing plug. One aspect of the present disclosure is directed to the use of a cam structure in a vascular closure device as part of an automatic or semi-automatic driving assembly. The cam structure may contact or be coupled to a compaction member assembly that is used to compact the sealing plug. The compaction member assembly may include a compaction tube that is arranged to contact the sealing plug. The compaction member assembly may also include a compaction tube driver positioned between the compaction tube and the cam structure. The cam structure may include at least one cam surface, and rotation of the cam structure contacts the cam surface with compaction tube driver to advance the compaction tube. The cam member may be coupled to a spool about which a portion of a suture is wound, wherein the suture is used to connect the sealing plug and an anchor of the vascular closure device together. The cam member may apply a variable driving force to the proximal end of the compaction assembly upon rotation of the spool. In some arrangements, the cam member is constructed as a driving plate that is arranged coaxially with the spool and is rotated upon rotation of the spool. A clutch may be operable between the driving plate and spool.

While the vascular instruments shown and described below include procedure sheaths and puncture sealing devices, the application of principles described herein are not limited to the specific devices shown. The principles described herein may be used with any medical device. Therefore, while the description below is directed primarily to arterial procedures and certain embodiments of a vascular closure device, the methods and apparatus are only limited by the appended claims.

As used in this specification and the appended claims, the terms "compact," "compaction," and "compacting" are used broadly to mean packing down and compressing by one or a succession of blows or taps or smooth, steady pressure, but not by excessive force. The terms "tamp" and "tamping" may relate to certain types or forms of "compaction" and "compacting." "Engage" and "engabable" are also used broadly to mean interlock, mesh, or contact between two devices. Likewise "disengage" or "disengagable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as used in the specification, including the claims, have the same meaning as the word "comprising."

Referring to FIGS. 1-4, a vascular closure device 100 is shown according to the prior art. Some example closure devices are disclosed in U.S. Published Patent Application No. 2005/0085851 and U.S. Pat. Nos. 7,618,438 and 7,618,436, which references are incorporated herein in their entirety by this reference. The vascular closure device 100 includes a carrier tube 102 with a filament or suture 104 extending at least partially therethrough. The vascular closure device 100 also includes a first or proximal end 106 and a second or distal end 107. External to the distal end 107 of the carrier tube 102 is an anchor 108. The anchor may include an elongated, stiff, low profile member including an eye 109 formed at the middle. The anchor 108 is typically made of a biologically resorbable polymer.

The suture 104 is threaded through the anchor 108 and back to a collagen pad 110. The collagen pad 110 may comprise, for example, randomly oriented fibrous material bound together by chemical means. The collagen pad 110 is slidingly attached to the suture 104 as the suture passes distally through the carrier tube 102. As the suture traverses the anchor 108 and reenters the carrier tube 102, the suture 104 is securely slip knotted proximal to the collagen pad 110 to facilitate cinching of the collagen pad 110 when the vascular closure device 100 is properly placed and the anchor 108 deployed (see FIG. 4).

The carrier tube 102 typically includes a compaction member 112 disposed therein. The compaction member 112 is slidingly mounted on the suture 104 and may be used by an operator to compact the collagen pad 110 toward the anchor 108 at an appropriate time to seal a percutaneous tissue puncture.

Prior to deployment of the anchor 108 within a vessel (e.g., an artery), the eye 109 of the anchor 108 rests outside the distal end 107 of the carrier tube 102. The anchor 108 may be temporarily held in place flush with the carrier tube 102 using a bypass tube 114 that is disposed over the distal end 107 of the carrier tube 102.

Figure 2:
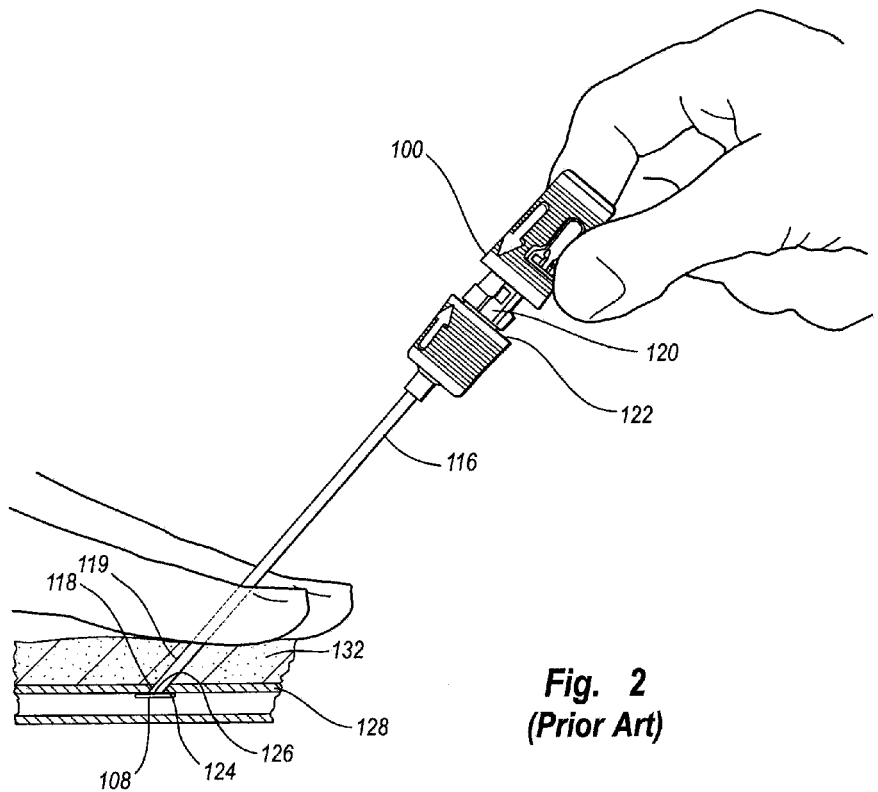
FIG. 2 is a side view of the tissue puncture closure device of FIG. 1 engaged with a vessel according to the prior art.
Figure 3:
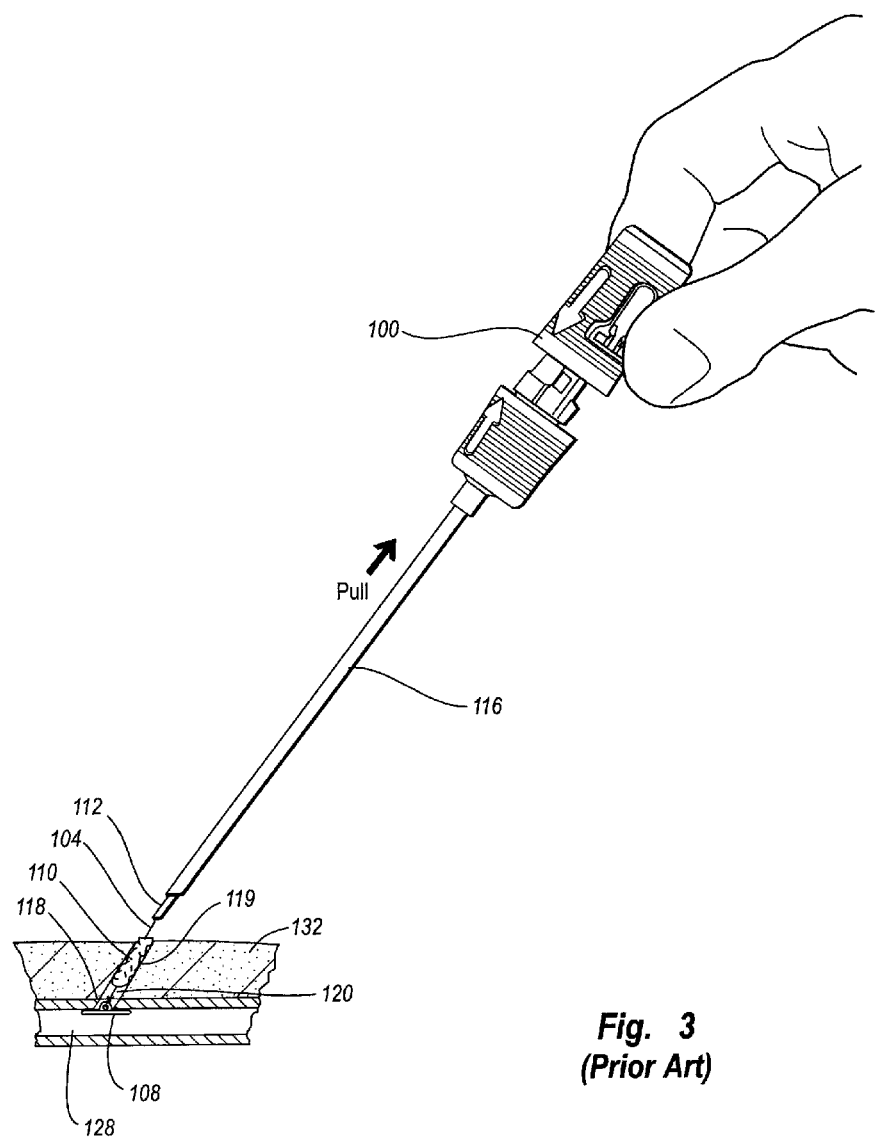
FIG. 3 is a side view of the tissue puncture closure device of FIG. 1 being withdrawn from a vessel according to the prior art to deploy a sealing plug.
Figure 4:
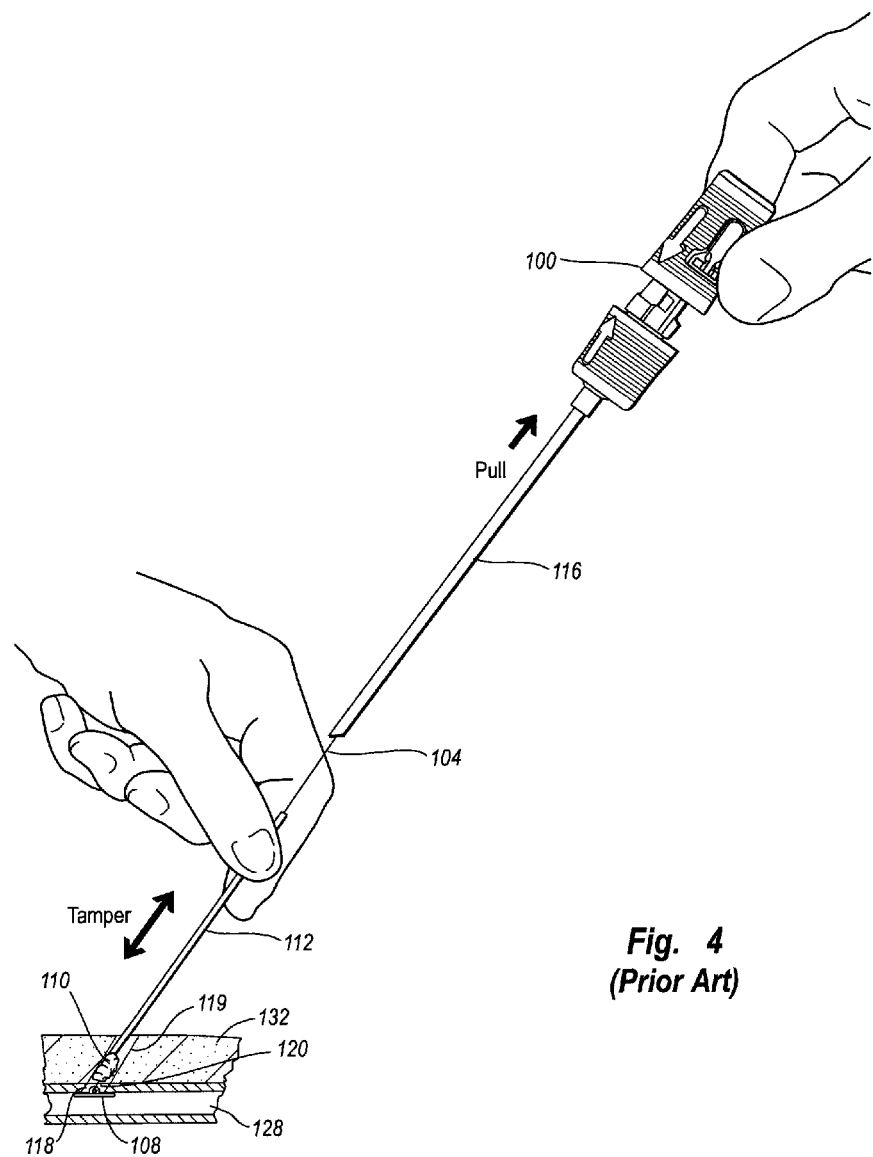
FIG. 4 is a side view of the tissue puncture closure device of FIG. 1 illustrating compaction of the sealing plug according to the prior art.

The flush arrangement of the anchor 108 and carrier tube 102 allows the anchor 108 to be inserted into a sheath such as insertion sheath 116 as shown in FIGS. 2-4, and eventually through a tissue (e.g., arterial) puncture 118. The insertion sheath 116 is shown in FIGS. 2-4 inserted through a percutaneous incision 119 and into a vessel 128. The bypass tube 114 (see FIG. 1) includes an oversized head 120 that prevents the bypass tube 114 from passing through an internal passage of the insertion sheath 116. As the vascular closure device 100 is inserted into the insertion sheath 116, the oversized head 120 bears against a surface 122 of insertion sheath 116.

Further insertion of the vascular closure device 100 results in sliding movement between the carrier tube 102 and the bypass tube 114, thereby releasing the anchor 108 from the bypass tube 114 (see FIG. 1). The anchor 108 typically remains in the flush arrangement shown in FIG. 1 following release from the bypass tube 114, limited in movement by the insertion sheath 116.

The insertion sheath 116 may include a monofold at a second or distal end 126 thereof. The monofold acts as a one-way valve to the anchor 108. A monofold is typically a plastic deformation in a portion of the insertion sheath 116 that elastically flexes as the anchor 108 is pushed out through the distal end 126 of the insertion sheath 116. Typically, after the anchor 108 passes through the distal end 126 of the insertion sheath 116 and enters the vessel 128, the anchor 108 is no longer constrained to the flush arrangement with respect to the carrier tube 102 and it deploys and rotates to the position shown in FIG. 2.

The insertion sheath 116 may include a pair of closure device connection apertures (not shown) and a carrier tube aperture (not shown) at a proximal surface 122 (see FIG. 1). The carrier tube 102 is inserted into the carrier tube aperture and the sheath connection members 130 are inserted into and releaseably engage with the closure device connection apertures when assembling the vascular closure device 100 with the insertion sheath 116.

Referring next to FIGS. 3-4, with the anchor 108 deployed, the vascular closure device 100 and the insertion sheath 116 are withdrawn together, ejecting the collagen pad 110 from the carrier tube 102 into the percutaneous incision 119 and exposing the compaction member 112. With the compaction member 112 fully exposed as shown in FIG. 4, the collagen pad 110 is manually compacted, and the anchor 108 and collagen pad 110 are cinched together and held in place with the self-tightening slip-knot on the suture 102. The tissue puncture is sandwiched between the anchor 108 and the collagen pad 110, thereby sealing the tissue puncture 118. The suture 104 is then cut and the percutaneous incision 119 may be closed. The suture 104, anchor 108, and collagen pad 110 are generally made of resorbable materials and therefore remain in place while the tissue puncture 118 heals.

It may be difficult to eject and compact the collagen pad 110 using the typical vascular closure device 100 described above. The insertion sheath 116 resists deformation as the collagen pad 110 is ejected from the carrier tube and compaction does not commence until the insertion sheath 116 has been removed so as to expose the compaction member 112 for manual grasping. Under certain conditions, removal of the insertion sheath 116 prior to compacting the collagen pad 110 causes the collagen pad 110 to retract or displace proximally from the tissue puncture 118, creating an undesirable gap between the collagen pad 110 and the tissue puncture 118.

The general structure and function of tissue puncture closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

Referring now to FIGS. 5A-5I, an apparatus, for example a tissue puncture closure device 200, is shown according to one embodiment of the present disclosure. The closure device 200 is shown in an assembly view in FIG. 5A. FIGS. 5B-5I illustrate the closure device 200 assembled and inserted through a procedure sheath 216 and into a lumen 232. The closure device 200 has particular utility when used in connection with intravascular procedures, such as angiographic dye injection, cardiac catheterization, balloon angioplasty and other types of recanalizing of atherosclerotic arteries, etc. as the closure device 200 is designed to cause immediate hemostasis of the blood vessel (e.g., arterial) puncture. However, it will be understood that while the description of the preferred embodiments below are directed to the sealing off of percutaneous punctures in arteries, such devices have much more wide-spread applications and may be used for sealing punctures or incisions in other types of tissue walls as well. Thus, the sealing of a percutaneous puncture in a vessel, shown herein, is merely illustrative of one particular use of the closure device 200 according to principles of the present disclosure.

The closure device 200 includes a first or proximal end portion 206 and a second or distal end portion 207. A carrier tube 202 extends from the proximal end portion 206 to the distal end portion 207 and includes an outlet 213 at the distal end portion 207. The distal end portion 207 may include a slit 209.

The carrier tube 202 may be made of plastic or other material and is designed for insertion through the procedure sheath 216. The procedure sheath 216 is designed for insertion through a percutaneous incision 219 in a tissue layer 230 and into the lumen 232. According to FIGS. 5B-5I, the lumen 232 comprises an interior portion of a vessel 228 (e.g., a femoral artery).

At the distal end portion 207 of the carrier tube 202 there is an anchor 208 and a sealing plug 210. The anchor 208 of the present embodiment is an elongated, stiff, low-profile member arranged to be seated inside the vessel 228 against a vessel wall 234 contiguous with a tissue puncture 218. The anchor 208 is preferably made of a biologically resorbable polymer. The sealing plug 210 is formed of a compressible sponge, foam, or fibrous mat made of a non-hemostatic biologically resorbable material such as collagen, and may be configured in any shape so as to facilitate sealing the tissue puncture 218.

Figure 5A:
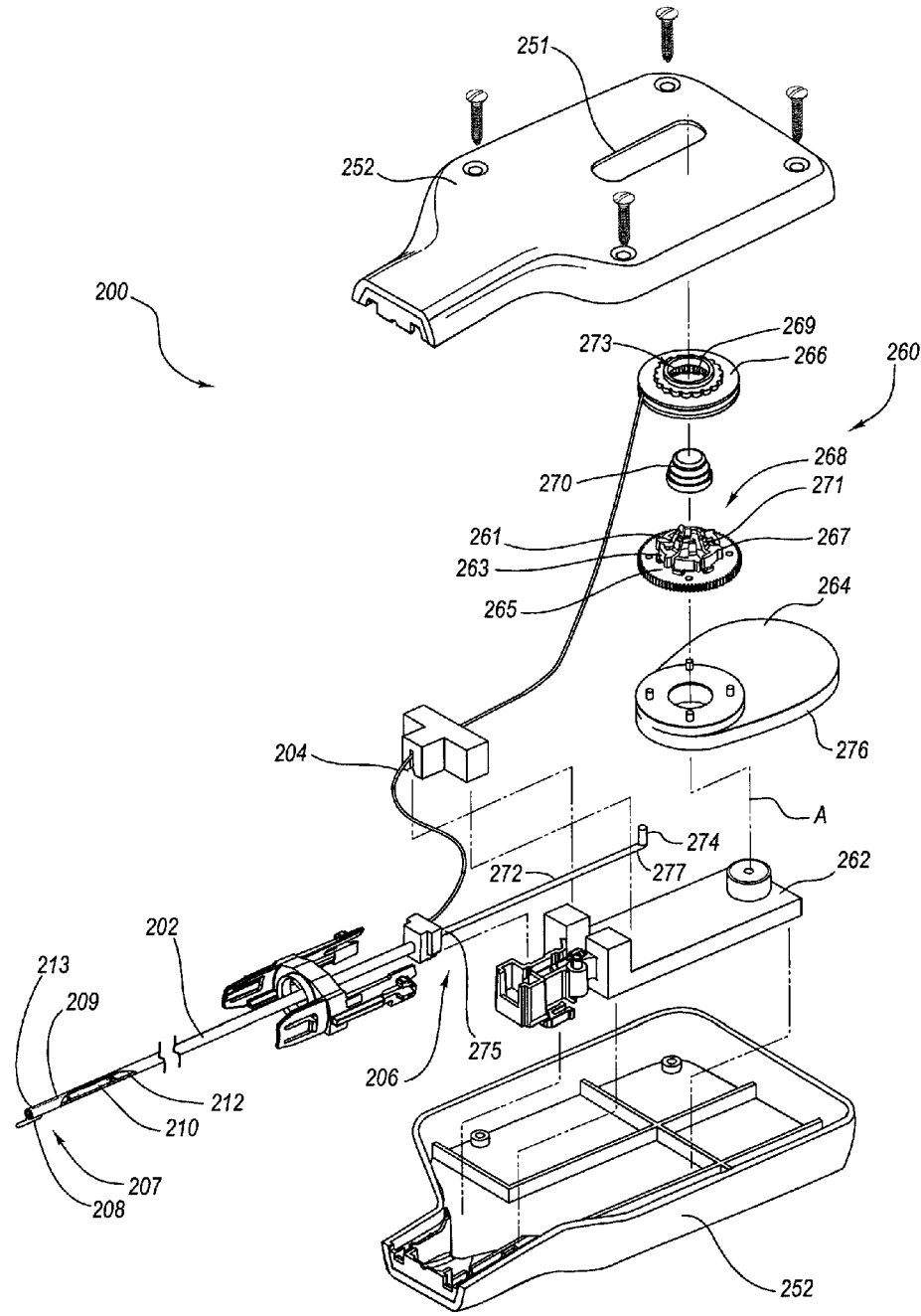
FIG. 5A is an exploded perspective view of an example tissue puncture closure device with an automatic compaction or driving mechanism according to the present disclosure.

The sealing plug 210 and anchor 208 are connected to one another by a connector such as a filament or suture 204 that is also biologically resorbable. The anchor 208, the sealing plug 210, and the suture 204 may be collectively referred to as the "closure elements" below. As shown in FIG. 5A, the anchor 208 is initially arranged adjacent to and exterior of the distal end portion 207 of the carrier tube 202, while the sealing plug 210 is initially disposed within the carrier tube 202. The anchor 208 is shown nested in its low profile configuration along the carrier tube 202 to facilitate insertion into the lumen 232 in FIG. 5A, and deployed abutting the vessel wall 234 in FIGS. 5B-5I.

The suture 204 extends distally from the proximal end portion 206 of the closure device 200 through the carrier tube 202. The suture 204 may be threaded through one or more perforations in the sealing plug 210, through a hole in the anchor 208, and proximally back toward the carrier tube 202 to the sealing plug 210. The suture 204 is preferably threaded again through a perforation or series of perforations in the sealing plug 210. The suture 204 may also be threaded around itself to form a self-tightening slip-knot. The suture 204 may thus connect the anchor 208 and the sealing plug 210 in a pulley-like arrangement to cinch the anchor 208 and the sealing plug 210 together when the carrier tube 202 is pulled away from the anchor 208 and the sealing plug 210. The anchor 208 and the sealing plug 210 sandwich and lock together with the suture 204, sealing the tissue puncture 218.

The carrier tube 202 may house a compaction device or compaction member, such as a compaction tube 212, for advancing the sealing plug 210 along the suture 204 and toward the anchor 208. The compaction tube 212 is shown located partially within the carrier tube 202 and proximal of the sealing plug 210. The compaction tube 212, however, may also extend through a handle or housing 252 of the closure device 200. The compaction tube 212 is preferably an elongated tubular or semi-tubular member that may be rigid or flexible and formed of any suitable material. For example, according to one embodiment, the compaction tube 212 is made of polyurethane. The suture 204 extends through at least a portion of the compaction tube 212. For example, as shown in FIGS. 5A-5I, the suture 204 extends along the compaction tube 212 between the proximal and distal end portions 206, 207. However, the suture 204 is not directly connected to the compaction tube 212. Accordingly, the suture 204 and the compaction tube 212 may slide past one another.

According to the embodiment of FIGS. 5A-5I, the suture 204 attaches to an automatic driving assembly 260. The automatic driving assembly 260 may include a base 262, a driving plate 264, a spool 266, and a clutch 268. The driving plate 264 includes a cam feature such as a cam surface 276. The cam surface 276 may be defined around a periphery surface of the driving plate 264. The cam surface 276 may include a curved or contoured portion. Portions of the cam surface 276 may track a circular curvature. Other portions of the cam surface 276 may track an elliptical, oblong, or other shaped curvature. Typically, the cam surface 276 has a change of curvature (i.e., a change of radius) along its length that provides a cam action when contacted and followed by a cam follower.

The driving plate 264, spool 266, clutch 268, and release member 270 may rotate about a common rotation axis A (see FIG. 5A). FIGS. 5A-5I illustrate a driving plate 264, spool 266 and clutch 268 that rotate counter clockwise about the rotation axis A. The cam surface 276 is typically not concentric about the rotation axis A (i.e., driving plate 264 is eccentrically mounted relative to rotation axis A). As the driving plate 264 rotates, the construction of the cam surface 276 provides driving of the compaction tube 212 with a variable driving or compaction force. A rotational force provided by unwinding the suture 204 from the spool 266 is translated into the variable driving or compaction force at an interface between the cam surface 276 and the compaction assembly (e.g., at least one of the compaction tube 212 and the compaction tube driver 272 described below).

The automatic driving assembly 260 may also include a release member 270 and a compaction tube driver 272. The release member 270 may extend through a release member opening or slot 251 of the housing 252 to be accessible by an operator of the closure device 200. The release member opening 251 may be sized to permit some longitudinal movement of the release member 270 relative to the housing 252. Actuation of the release member 270 may permit free unwinding of the suture 204 from the spool 266 without further compacting of the sealing plug 210.

The compaction tube driver 272 includes distal and proximal ends 275, 277. The distal end 275 may abut the compaction tube 212 (e.g., at a proximal end of the compaction tube 212). A driver follower 274 may be positioned at the proximal end 277 of the compaction tube driver 272. The driver follower 274 may be arranged in the housing 252 adjacent the cam surface 276 so that rotation of the driving plate 264 results in contact between the cam surface 276 and the driver follower 274. The cam construction of cam surface 276 results in application of a linear force to the compaction tube driver 272 through the driver follower 274 to advance the compaction tube 212 toward the sealing plug 210.

In some arrangements, the automatic driving assembly 260 may include the compaction tube 212. The compaction tube 212 and compaction tube drive 272 may together define a compaction tube assembly. The compaction tube assembly may be positioned proximal of and adjacent to the sealing plug 210. The entire automatic driving assembly 260, including the compaction tube 212, may move together longitudinally relative to the housing 252.

The automatic driving assembly 260 may be located within the housing or housing 252 at the proximal end portion 206 of the closure device 200. Embodiments of the automatic driving assembly 260 may be selectively disengagable. For example, operation of the release member 270, which is accessible through the release member opening 251 in the housing 252, may release the spool 266 to permit unspooling of the suture 204. Unspooling of the suture 204 after compaction of the sealing plug 210 permits the operator to cut the suture at a location proximal of the sealing plug 210.

As shown in FIG. 5A, the driving plate 264 may be connected to the spool 266. The suture 204 is connected to and partially wound about the spool 266. The driving plate 264 tends to rotate at the same angular rate as the spool 266. A clutch 268 may selectively connect and release the driving plate 264 relative to the spool 266. One embodiment of the clutch 268 is described in detail below. However, any clutch may be operable between the driving plate 264 and spool 266.

Withdrawal of the closure device 200 from the tissue puncture 218 (if the anchor 208 is deployed and the automatic driving assembly 260 has contacted the stop (see FIGS. 5F and 5H)) causes the suture 204 to unwind from the spool 266. The spool 266 rotates as the suture 204 unwinds and provides a torsional motive force that is transduced to a linear compaction force.

The torsional motive force provided by the spool 266 is transduced into the linear compaction force interaction between the driving plate 264 and compaction tube driver 272. The driving plate 264 may be arranged coaxially with the spool 266. When the spool 266 rotates, it drives the driving plate 264, which in turn drives the compaction tube driver 272. The compaction tube driver 272 drives the compaction tube 212, which in turn compacts the sealing plug 210.

The compaction tube 212 is preferably tubular or semi-tubular and partially disposed about the suture 204 along its longitudinal axis. The compaction tube driver 272 may comprise at least portions of the compaction tube 212. The compaction tube driver 272 may comprise a semi-tubular shape having a generally U-shaped cross section, to provide a trough through which the suture 204 may enter and exit laterally. An open trough would permit the suture and the compaction tube driver 272 to merge as the spool 266 unwinds. Accordingly, with the anchor 208 deployed, as the closure device 200 is retracted in a first direction the suture 204 unwinds from the spool 266, which drives the driving plate 264. The driving plate 264 drives the compaction tube driver 272 and the compaction tube driver 272 drives the compaction tube 212 in a second direction that is opposite the first direction. The compaction tube 212 compacts the sealing plug 210.

Figures 5B, 5C:
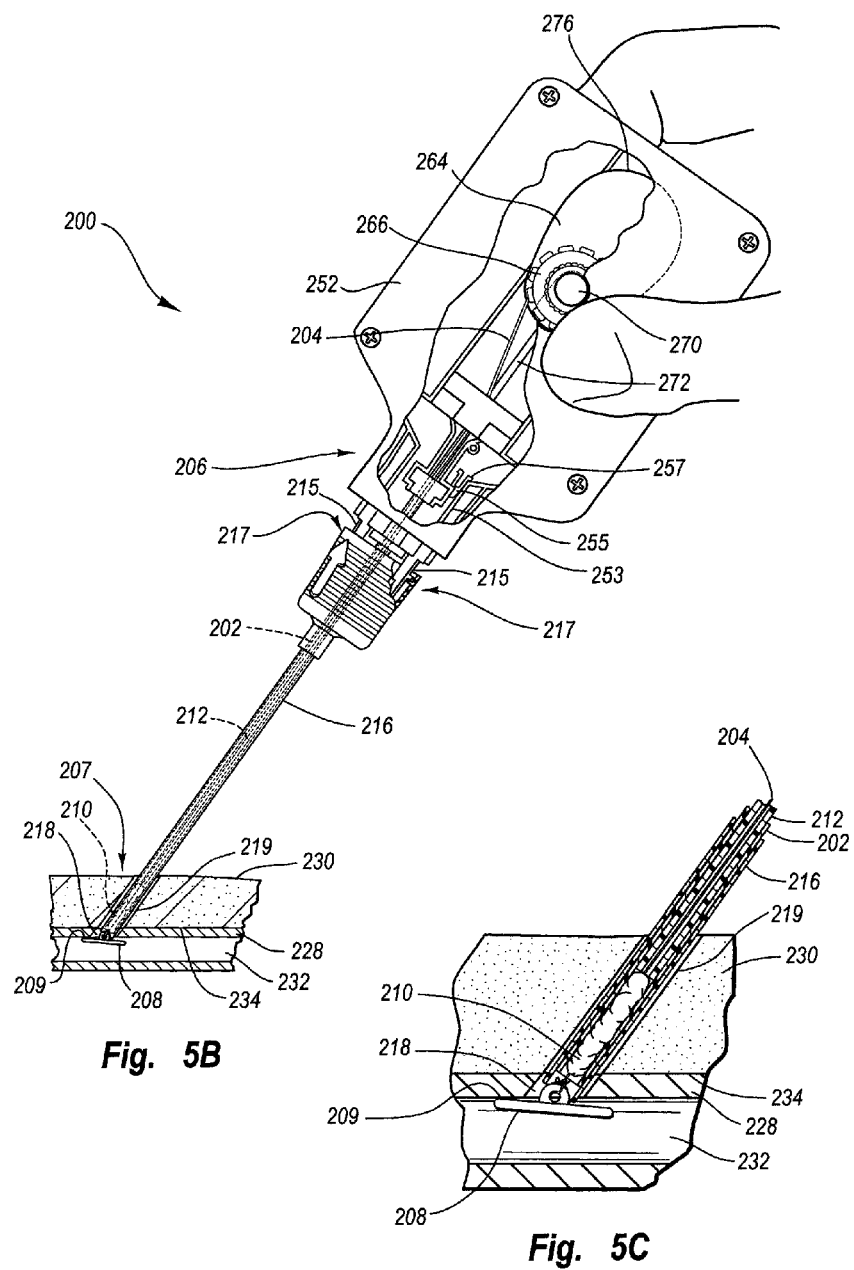
FIG. 5B is a side view of the tissue puncture closure device of FIG. 5A inserted through a procedure sheath and tissue puncture and engaged with a vessel in a first position.
FIG. 5C is a detailed inset of FIG. 5B.

In practice, the carrier tube 202 of the closure device 200 (containing the closure elements described above) is inserted into the procedure sheath 216, which is already inserted within the vessel 228 (see FIGS. 5B-5C). As the closure device 200 and the associated closure elements are inserted into the procedure sheath 216, the anchor 208 passes through and out of the distal end of the procedure sheath 216 and is inserted into the lumen 232. As mentioned above and shown in FIG. 5A, the anchor 208 is initially arranged substantially flush with the carrier tube 202 to facilitate insertion of the anchor 208 through the percutaneous incision 219 and into the lumen 232.

After the anchor 208 passes out of the distal end of the procedure sheath 216, however, the anchor 208 tends to deploy or rotate to the position shown in FIGS. 5B-5C. The closure device 200 may be partially withdrawn from the procedure sheath 216, catching the anchor 208 on the distal end of the procedure sheath 216 and rotating the anchor 208 into the position shown in FIGS. 5B-5C. The closure device 200 preferably includes a pair of biased fingers 215 that are lockingly received by a matching pair of recesses 217 in the procedure sheath 216. The locking arrangement between the biased fingers 215 and matching recesses 217 may fix the position of the housing 252 relative to the procedure sheath 216.

Figures 5D, 5E:
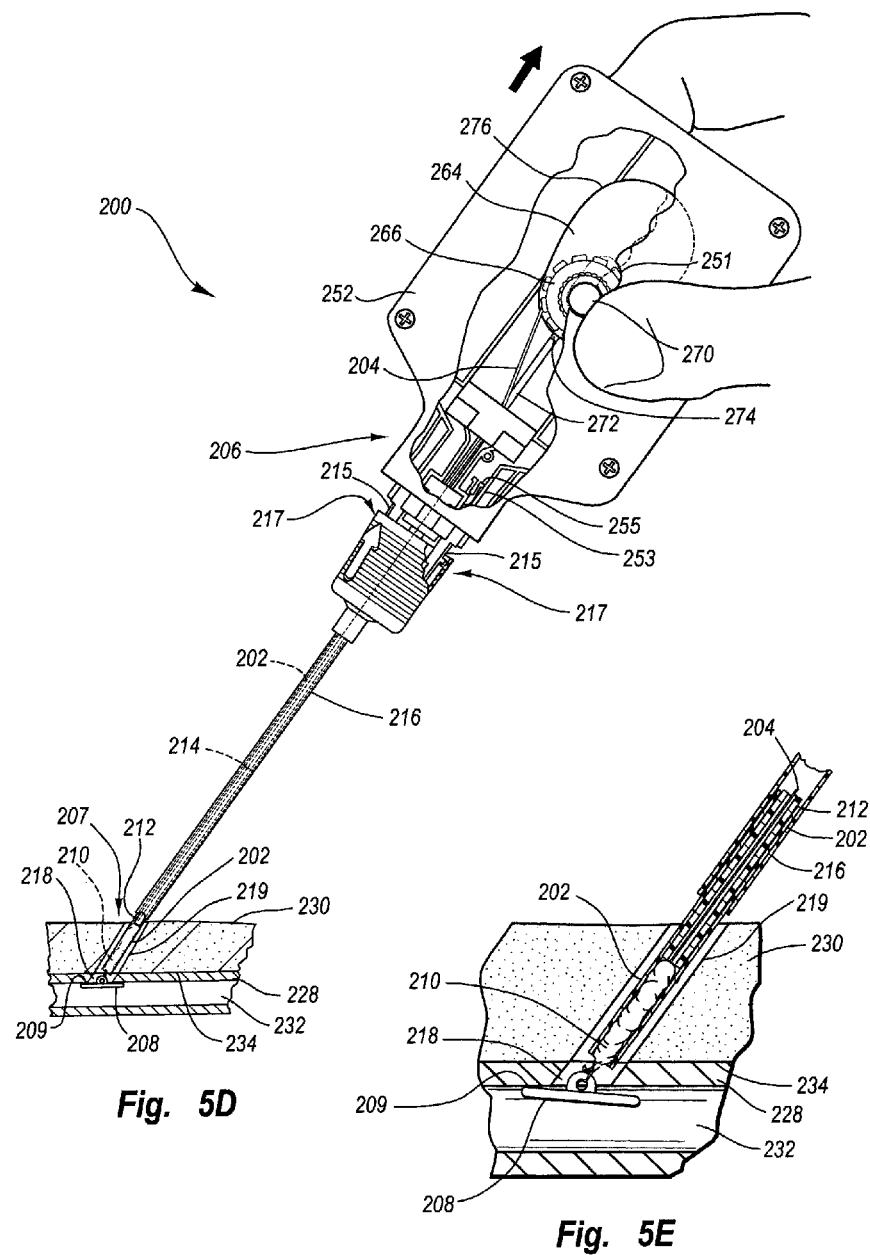
FIG. 5D is a side view of the tissue puncture closure device of FIG. 5A shown engaged with a vessel in a second position with the procedure sheath retracted.
FIG. 5E is a detailed inset of FIG. 5D.

Following deployment of the anchor 208, the housing 252 and the procedure sheath 216 are withdrawn together. Withdrawing the housing 252 causes the anchor 208 to anchor itself within the vessel 228 against the vessel wall 234 as shown in FIGS. 5B-5C. Further withdrawing the housing 252 causes the automatic driving assembly 260 to slide forward in the housing 252 as shown in FIG. 5D-5E. Functionally, the anchor 208, sealing plug 210, carrier tube 202, procedure sheath 216, and automatic driving assembly 260 maintain the same axial position upon this further withdrawal of the housing 252, and the procedure sheath 216 and housing 252 move proximally (see FIGS. 5D-5E).

Referring to FIGS. 5D-5E, the distal end portion 207 of the carrier tube 202 is exposed within the percutaneous incision 219 as the housing 252 and the procedure sheath 216 are retracted. The carrier tube 202 may retain its position relative to the tissue puncture 218 until the housing 252 and the procedure sheath 216 have been retracted a predetermined distance. Relative movement between the housing 252/procedure sheath 216 and the carrier tube 202 may be facilitated by a sliding mount arrangement between the automatic driving assembly 260 and the housing 252. However, according to some embodiments the automatic driving assembly 260 is fixed to the housing 252.

As shown by the combination of FIGS. 5B-5I, the automatic driving assembly 260, which is attached to the carrier tube 202, may be free floating or displaceable and slides relative to the housing 252 as the housing 252 and the procedure sheath 216 are retracted. However, the automatic driving assembly 260 may be initially held in a first position relative to the housing 252, as shown in FIG. 5B. For example, as shown in FIG. 5B, the automatic driving assembly 260 may comprise a temporary holder such as a stowage detent 255 slidingly mounted in a track. The track is shown in FIG. 5B as a webbing track 253. The webbing track 253 is disposed in the housing 252. The stowage detent 255 may include a finger 257 with a protrusion to at least temporarily hold the automatic driving assembly 260 in the first position shown in FIG. 5B, and prevent premature sliding within the housing 252.

Although the finger 257 tends to hold or temporarily lock the automatic driving assembly 260 in the first position shown in FIG. 5B, the finger 257 releases when a sufficient force is applied between the housing 252 and the automatic driving assembly 260. For example, with the anchor 208 deployed, a retraction force provided by a user to the housing 252 causes the finger 257 to deflect inward and release. Thereafter, the finger 257 provides very little resistance to sliding movement between the automatic driving assembly 260 and the housing 252. Accordingly, retraction of the housing 252 may retract the procedure sheath 216, which is fixedly connected to the housing 252, but the automatic driving assembly 260 and the carrier tube 202 may slide relative to the housing 252 and therefore remain in position with respect to the tissue puncture 218, as shown in FIG. 5D. The automatic driving assembly 260 may slide a predetermined distance with respect to the housing 252 until the automatic driving assembly 260 reaches a stop. The predetermined distance may be at least long enough to fully expose the slit 209 (see FIG. 5A) in the carrier tube 202 to facilitate later removal of the sealing plug 210 from the carrier tube 202.

When the automatic driving assembly 260 reaches the stop, further retraction of the housing 252 withdraws the carrier tube 202 as well, ejecting the sealing plug 210 automatically, as shown in FIGS. 5F-5G. The spool 266 begins to rotate to permit unwinding of some of the suture 204 from the spool. Typically, the driving plate 264, which rotates with the spool 266, unwinds an amount that does not initiate advancing of the compaction tube driver 272 and compaction tube 212. The driver follower 274 of the compaction tube driver 272 may track along that portion of the cam surface 276 that has a constant radius (see FIG. 5F), thereby avoiding substantial advancing of the compaction tube driver 272.

Still further retraction of the housing 252 further rotates the spool 266 and driving plate 264 to contact the variable radius portion (i.e., the increased radius portion) of the cam surface 276 with the driver follower 274 to advance the compaction tube driver 272. Advancing the compaction tube driver 272 advances the compaction tube 212 to compact the sealing plug 210 toward the anchor 208 (see FIGS. 5H-5I). Upon completion of compacting the sealing plug 210, the operator may actuate the release member 270 to permit unwinding of the suture 204 from the spool 266 so that the suture 204 may be cut near the tissue layer 230 to release the housing 252 from the anchor 208/sealing plug 210.

Unlike previous closure devices that require a separate, manual compaction procedure following the deposition of the sealing plug 210, the closure device 200 of the present disclosure automatically compacts the sealing plug 210 by applying a retracting force to the housing 252. The sealing plug 210 may be compacted during or after withdrawal of the carrier tube 202, reducing or eliminating gaps that may otherwise occur between the sealing plug 210 and the tissue puncture 218 in the vessel 228.

Figures 5H, 5I:
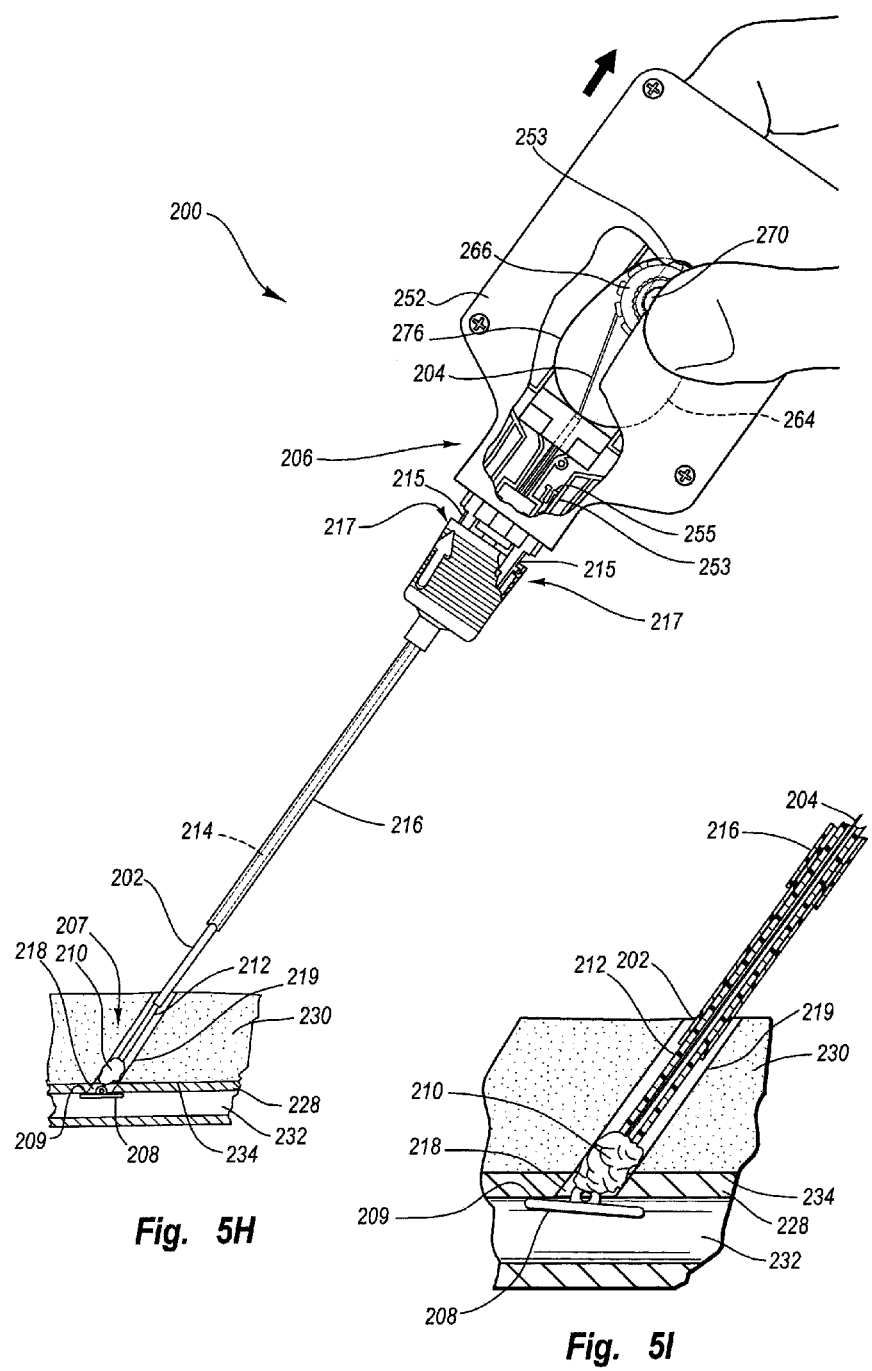
FIG. 5H is a side view of the tissue puncture closure device of FIG. 5A engaged with a vessel in a third fourth position compacting the sealing plug.
FIG. 5I is a detailed inset of FIG. 5H.

In addition, by placing tension on or pulling the suture 204 away from the percutaneous incision 219, the suture 204 may cinch and lock (with a slip knot or the like) together the anchor 208 and the sealing plug 210, sandwiching the vessel wall 234 between the anchor 208 and sealing plug 210. The force exerted by the compaction tube 212 and the cinching together of the anchor 208 and sealing plug 210 by the suture 204 also causes the sealing plug 210 to deform radially outward within the percutaneous incision 219 and function as an anchor on the proximal side of the tissue puncture 218 as shown in FIGS. 5H-5I.

Figures 6A, 6B, 6C:
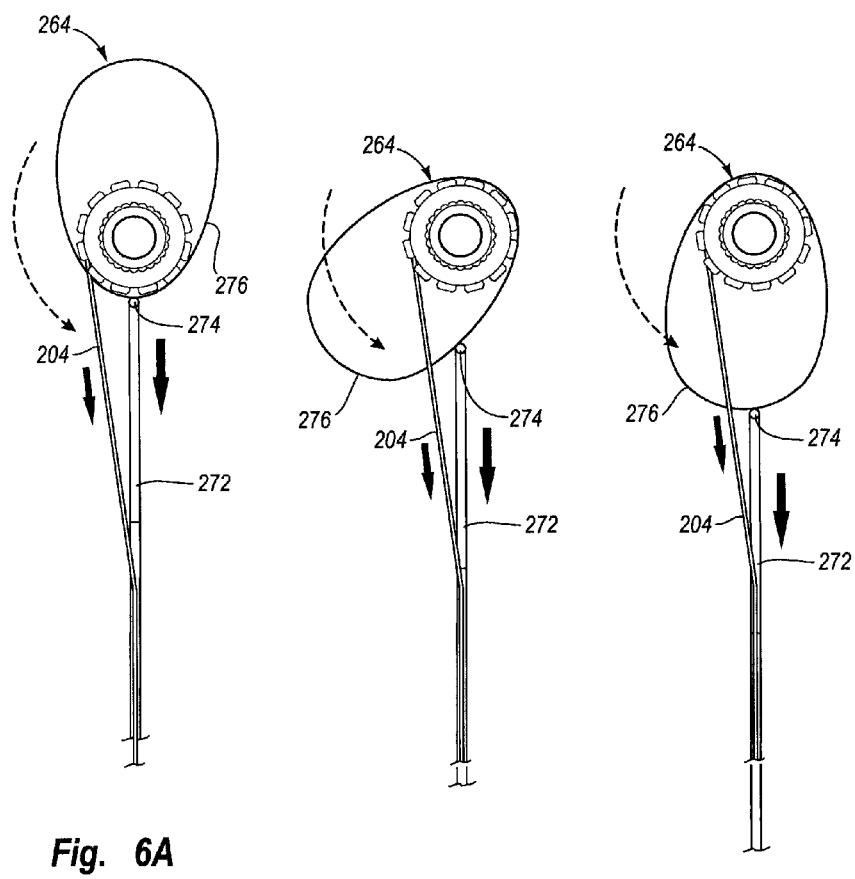
FIGS. 6A-6C illustrate a driving plate of the tissue puncture closure device of FIG. 5A in three different rotated positions to advance a compaction tube driver of the tissue puncture closure device.

The compaction tube 212 is automatically driven toward the sealing plug 210 by the automatic driving assembly 260. The driving plate 264 of the automatic driving assembly 260 is shown in further detail in FIGS. 6A-6C. The driving plate 264 advances the compaction tube driver 272 by contact between the cam surface 276 and the driver follower 274. Other arrangements are possible for transferring the rotational motion of the driving plate 264 to a linear force in the compaction tube driver 272. The use of a driver follower 274 extending from the end of an elongate compaction tube driver 272 and arranged to contact a cam surface 276 along a periphery of a driving plate 264 is merely exemplary. In other arrangements, the compaction tube driver 272 may be permanently connected to the driving plate 264. The driving plate 264 may be directly connected to the compaction tube 212. Generally, any device or construction that uses of a cam structure driven by rotation of a spool member (about which the suture is wound) either directly or indirectly to advance a compaction member to compact a sealing plug falls within the spirit and scope of the present disclosure.

In some arrangements, the automatic driving assembly may include a gear assembly or additional structure interposed between the spool member and driving plate. In some examples, the spool member and driving plate are not arranged coaxially. As such the driving plate may be indirectly driven or rotated by the spool member.

In embodiments including the clutch 268, the clutch 268 may comprise a plurality of release fingers 261 as shown in FIG. 5A. The release fingers 261 are arranged substantially in a circle. A first component 263 of the release fingers 261 is cantilevered from a base 265 and extends normal therefrom. A protrusion 267 of the first component 263 extends radially outward and is received by a mating internal recess 269 of the spool 266. A second component 271 of the release fingers 261 arcs substantially normal to the first component 263 and the base 265. The second component 271 of each of the release fingers 261 extends through a central hole 273 of the spool 266. The release member 270 fits over and contacts the second components 271 of each of the release fingers 261.

The fit of the protrusions 267 of the base 265 with the mating recesses 269 of the spool 266 causes the base 265 (and thus the driving plate 264 to which the base 265 is fixedly attached) and spool 266 to rotate together at an identical angular velocity. However, when the release member 270 is depressed, the release member 270 slides along the arcs of the second component 271, forcing each of the release fingers 261 radially inward. The radial inward displacement of the release fingers 261 at least partially removes the protrusions 267 from the mating recesses 269, allowing independent rotation of the spool 266 with respect to the driving plate 264. Therefore, after the sealing plug 210 is driven toward the anchor 208, the selectably disengagable automatic driving assembly 260 is disengaged or disabled, allowing the suture 204 to safely unwind without further compaction. The suture 204 is then exposed to the operator for convenient cutting.

Another embodiment of the a driving plate 364 is illustrated in FIGS. 7 and 8A-8C. The driving plate 364 includes a cam slot 378 that defines at least one cam surface 376. The cam slot 378 may have a shape that mirrors a cam shape of another portion of the driving plate 364, such as an outer periphery surface of the driving plate 364. Alternatively, the cam slot 378 may have a unique shape and size from the outer periphery shape of the driving plate 364. The cam slot 378 may have any shape, curvature, and length to provide the desired linear movement of the compaction tube driver 272 at a given rotated position of the driving plate 264.

The driver follower 274 of the compaction tube driver 272 may be inserted into the cam slot 378 and arranged in contact with at least one of the internal cam surfaces 376 defined along a length of the cam slot 378. Rotation of the driving plate 364, as shown in FIGS. 8A-8C, eventually advances the compaction tube driver 272. The use of a cam slot 378 may promote a more secure connection or interface between the compaction tube driver 272 and the driving plate 364.

Figure 9:
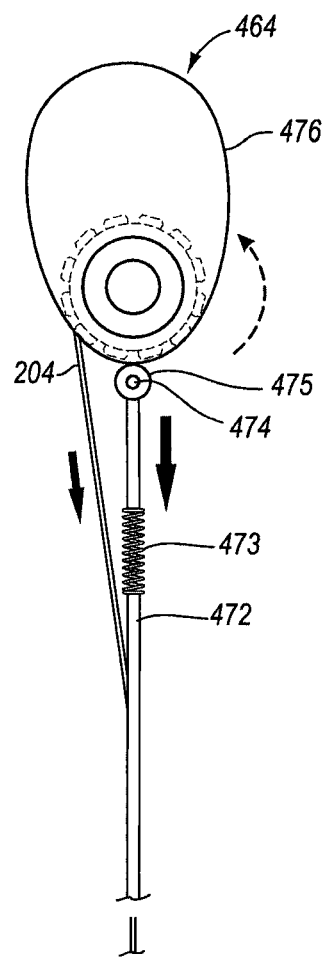
FIG. 9 illustrates the driving plate of FIG. 5A with another example compaction tube driver in accordance with the present disclosure.

Another embodiment of the a driving plate 464 and compaction tube driver 472 is illustrated in FIG. 9. The driving plate 464 includes a cam surface 476 and may be constructed similar to the driving plate 264 described above. The compaction tube driver 472 may include a clutch member 473 that limits overcompaction of the sealing plug of the tissue puncture closure device. The clutch member 473 may include, for example and without limitation, a biasing member such as a compression spring. The clutch member 473 may be positioned at any location along the length of the compaction tube driver 472, or along a length of the compaction tube or other feature driven by or integrated into the compaction tube driver 472. Multiple clutch members 473 may be used in series or in parallel to provide a clutch function in the compaction tube driver 472.

The compaction tube driver 472 may include a driver follower 474. The driver follower 474 may include a friction reducing member 475 that limits or reduces friction at an interface between the compaction tube driver 472 and the driving plate 464. In one arrangement, the friction reducing member 475 may include a roller, low friction pad, or bearing member of any shape, size or construction.

Operation of the embodiment of FIGS. 5A-6C is as follows with similar operation possible for the embodiment of FIGS. 8A-C. As the housing 252 of the closing device 200 is retracted from the percutaneous incision 219 with the anchor 208 secured within the vessel 228, as shown in FIG. 5B, the stowage detent 255 releases. The automatic driving assembly 260 and carrier tube 202 may remain stationary and therefore float relative to the housing 252. The procedure sheath 216 is retracted as the housing 252 is withdrawn, exposing the distal end portion 207 of the carrier tube 202. The automatic driving assembly 260 eventually contacts a stop (or, in some embodiments, the automatic driving assembly is fixed), and further retraction causes the automatic driving assembly 260 and carrier tube 202 to retract as well. As the automatic driving assembly 260 retracts, the suture 204, which is threaded through the anchor 208, unwinds from and causes rotation of the spool 266. The spool 266 drives the driving plate 264 as the spool 266 rotates via a coaxial connection therebetween.

As the driving plate 264 rotates, the cam surface 276 of the driving plate 264 contacts the driver follower 274 of the compaction tube driver 272 to drive the compaction tube 212. In some arrangements, the compaction tube driver 272 may be long enough and constructed such that it functions as the compaction tube 212. The compaction tube 212 compacts the sealing plug 210.

Therefore, as the closing device 200 is retracted from the percutaneous incision 219, the procedure sheath 216 may be retracted (see FIGS. 5D-5E), the carrier tube may be retracted (see FIGS. 5F-5G), and the sealing plug 210 is automatically compacted (see FIGS. 5H-5I). The sealing plug 210 is more likely to create a sufficient vascular seal without a gap relative to the anchor 208, as may otherwise occur with a separate manual compaction procedure.

Moreover, when the sealing plug 210 has been sufficiently compacted, the automatic driving assembly 260 may be disengaged, enabling further retraction of the closure device 200 without additional compaction. With the sealing plug 210 fully compacted, there may be little or no portion of the suture 204 extending outside of the tissue layer 230 and exposed to an operator. Therefore, it may be difficult for an operator to separate the sealing plug 210 and anchor 208 from the remainder of the closure device 200. In addition, too much retraction with the selectably automatic driving assembly 260 enabled could potentially overcompact the sealing plug 210 into the vessel 228. Accordingly, the automatic driving assembly 260 may be advantageously disabled by activating the release member 270 through the release member opening 251. Activating the release member 270 allows the suture 204 to fully unwind from the spool 266 without driving the compaction tube 212. Unwinding the spool 266 exposes a sufficient length of the suture 204 to allow an operator to easily cut the suture 204 and separate the sealing plug 210 and anchor 208 from the remainder of the closure device 200.

The preceding description has been presented only to illustrate and describe exemplary embodiments of the present disclosure. It is not intended to be exhaustive or to limit the invention to any precise form disclosed. Many modifications and variations are possible in light of the above teaching. It is intended that the scope of the invention be defined by the following claims.

What is claimed is:

1. A tissue puncture closure device, comprising:
   an anchor;
   a sealing plug;
   a filament positioned between the sealing plug and the anchor;
   a compaction member assembly structured and arranged to apply an axially directed compressive force to automatically compact the sealing plug toward the anchor, the compaction member assembly having a distal end and a proximal end;
   a spool having a portion of the filament wound thereon;
   an eccentric cam, the cam being eccentrically mounted relative to the spool, the cam having a cam surface portion, the cam surface portion being eccentric relative to a rotation axis of the cam, the cam surface portion being arranged to contact the compaction member assembly upon rotation of the spool to advance the distal end of the compaction member assembly.

2. A tissue puncture closure device according to claim 1 wherein the cam surface portion is defined around a periphery of the cam.

3. A tissue puncture closure device according to claim 1 wherein the cam surface portion is defined within a slot feature of the cam.

4. A tissue puncture closure device according to claim 1 wherein the compaction member assembly further includes a drive follower positioned at the proximal end of the compaction member assembly and exposed for contact by the cam surface portion.

5. A tissue puncture closure device according to claim 1 wherein the compaction member assembly includes a compaction tube and a compaction tube driver arranged end-to-end, the compaction tube defining the distal end of the compaction member assembly.

6. A tissue puncture closure device according to claim 1 wherein the cam surface portion includes a constant radius portion and a variable radius portion.

7. A tissue puncture closure device for partial insertion into and sealing of a tissue puncture in an internal tissue wall accessible through a percutaneous incision, comprising:
   an anchor for disposition on a distal side of the internal tissue wall;
   a sealing plug for disposition on a proximal side of the internal tissue wall;
   a filament connected to and anchored at a distal end to the anchor and sealing plug, the sealing plug being slidable and cinchable along the filament toward the anchor to close the tissue puncture;
   a compaction assembly disposed on the filament and arranged to drive the sealing plug along the filament distally towards the anchor; the compaction assembly having a proximal end
   a storage spool onto which a proximal end of the filament is wound;
   an eccentric cam, the cam being eccentrically mounted relative to the storage spool, the cam having a cam surface arranged to apply a variable driving force to the proximal end of the compaction assembly upon rotation of the storage spool, the cam surface being eccentric relative to a rotation axis of the cam.

8. A tissue puncture closure device of claim 7 wherein the cam is connected to the storage spool by a releasable clutch.

9. A tissue puncture closure device of claim 7 wherein the cam surface comprises a constant radius portion and a variable radius portion.

10. A tissue puncture closure device of claim 7 wherein the storage spool and cam are arranged coaxially.

11. A tissue puncture closure device of claim 7 wherein the cam is coupled to the compaction assembly.

12. A tissue puncture closure device of claim 7 wherein withdrawal of the tissue puncture closure device from the tissue puncture with the anchor bearing against the internal tissue wall unwinds the filament from the storage spool.

13. A tissue puncture closure device of claim 12, wherein the storage spool rotates the cam, and the cam drives the compaction assembly to directly or indirectly provide a compaction force to the sealing plug.

14. A tissue puncture closure device of claim 7, wherein the cam surface directly contacts the compaction assembly.

* * * * *